United States Patent [19]

Dann et al.

[11] Patent Number: 5,752,944
[45] Date of Patent: May 19, 1998

[54] MALE INCONTINENCE DEVICE

[76] Inventors: Jeffrey A. Dann, 44 Terrace Dr., Worcester, Mass. 01609; David A. Gloth, 16 Harcourt St., Boston, Mass. 02116

[21] Appl. No.: 728,258

[22] Filed: Oct. 8, 1996

[51] Int. Cl.⁶ .................................................. A61F 5/44
[52] U.S. Cl. .................................... 604/352; 604/349
[58] Field of Search .............................. 604/329–331, 604/349–353

[56] References Cited

U.S. PATENT DOCUMENTS

| | | | |
|---|---|---|---|
| 4,652,259 | 3/1987 | O'Neil | 604/54 |
| 4,710,169 | 12/1987 | Christopher | 604/104 |
| 4,963,137 | 10/1990 | Heyden | 604/349 |
| 5,074,314 | 12/1991 | Wilson | 128/844 |
| 5,195,998 | 3/1993 | Abraham et al. | 604/351 |
| 5,242,391 | 9/1993 | Place et al. | 604/60 |
| 5,263,947 | 11/1993 | Kay | 604/349 |
| 5,306,226 | 4/1994 | Salama | 600/29 |
| 5,334,175 | 8/1994 | Conway et al. | 604/352 |
| 5,366,449 | 11/1994 | Gilberg | 604/349 |
| 5,380,312 | 1/1995 | Goulter | 604/352 |
| 5,409,475 | 4/1995 | Steer | 604/353 |
| 5,415,179 | 5/1995 | Mendoza | 128/842 |
| 5,417,666 | 5/1995 | Coulter | 604/172 |
| 5,445,626 | 8/1995 | Gigante | 604/349 |

OTHER PUBLICATIONS

Article entitled "Bardex I.C.—Foley Catheter", Bard Urological Division, C.R. Bard, Inc. (Date Unknown—Not admitted to be prior art) © Jan. 1995.
Article entitled "Bard Cunningham Incontinence Clamp", Bard Patient Care Division, C.R. Bard, Inc. (Date Unknown—Not admitted to be prior art) © Apr. 1992.

*Primary Examiner*—Robert A. Clarke
*Attorney, Agent, or Firm*—Judith C. Crowley; Nutter, McClennen & Fish LLP

[57] ABSTRACT

A two piece male incontinence device includes an inner sheath adapted to adhere to and cover at least a portion of the penis of the user and an outer sheath adapted to adhere to the inner sheath and to direct voided urine to a receptacle. At least the penile meatus is exposed through an opening in the inner sheath. The outer sheath includes a continuous cap-like section adapted to adhere to the inner sheath, a urine collection section and a tube section suitable for connection to a urine receptacle. The user changes the outer sheath as needed while leaving the inner sheath intact for prolonged periods of time, thereby minimizing penile skin damage and erosion resulting from repeated removal of a device adhesively bonded to the skin.

22 Claims, 8 Drawing Sheets

MALE INCONTINENCE DEVICE

FIELD OF THE INVENTION

The present invention relates generally to external devices for preventing male urinary incontinence and, in particular, to devices which channel urinary discharge into urine collection receptacles.

BACKGROUND OF THE INVENTION

There are over two million men in the United States who suffer from urinary incontinence. Urinary incontinence may result from a variety of diseases including neurologically impaired bladder function, mental deterioration such as Alzheimer's disease and prostate obstruction. Prostate surgery, including radical prostatectomy and transurethral resection of the prostate, can also result in transient or permanent incontinence in men. Men wishing to prevent urinary leakage have been relegated to two solutions: external catheter-type collection systems or crude clamping devices.

Clamping devices are placed across the shaft of the penis to occlude urine flow. Unfortunately, these devices can restrict circulation to the distal end of the penis, thereby requiring the user to remove the clamp several times a day to allow proper blood flow. In addition to the penile discomfort from the clamp, the size of these devices makes them cosmetically unattractive.

External male urinary catheter collection systems, or condom catheters, generally are comprised of an elongated, circularly tubular sheath of one piece construction having a forward position defining a fluid passage tube, a conical midsection providing a forward discharge opening in communication with the fluid passage tube and a thin wall rearward portion adapted for extending over the shaft of the penis. The rearward portion has an adhesive substance on its inner wall surface to adhere to the penile shaft in a liquid tight seal. The conical midsection portion of the device may have a dilated area which serves as a surge chamber for voided urine. To function correctly, the tip of the penis is positioned in close space-relation to the forward discharge opening and the rearward portion is unrolled onto the penile shaft.

One such condom catheter is disclosed in U.S. Pat. No. 4,963,137 to Heyden as a one piece device constructed of a resilient material. The Heyden device has a rearward portion adapted to loosely receive the penile shaft. The device is then adhesively attached to the penile shaft in a liquid tight seal by fittingly molding the rearward portion about the penis. Another condom catheter is disclosed in U.S. Pat. No. 5,334,175 to Conway et al. as a one piece device with a cone-shaped rearward section having adhesive on the inner surface. The rearward section unrolls over and adheres to the shaft of the penis and is intended for males having a recessed penis.

Unfortunately, difficulties with proper positioning and poor fit are common problems associated with condom catheters. The flexibility of the penile skin often causes the penile tip to fall backward or forward, thereby blocking the forward discharge opening to the fluid passage tube, thus causing improper positioning and hindering the function of the device. Furthermore, the frequent need to change the condom catheter for sanitary reasons leads to skin damage, abrasions, and erosions when the device is pulled away from the skin. The more frequent the changing of the device, the more likely that serious skin damage will occur from skin to adhesive bonding. Therefore, a device is needed that effectively collects urinary discharge while minimizing the potential for skin damage from frequent changes.

SUMMARY OF THE INVENTION

A two-piece male incontinence device includes an inner sheath sized and shaped to cover and adhere to at least a portion of the penis of the user and an outer sheath adapted to adhere to the inner sheath and to direct voided Urine to a urine receptacle. At least the meatus of the penis is exposed through an opening at the forward end of the inner sheath, permitting voided urine to be directed to the urine receptacle by the outer sheath.

The outer sheath includes a cap-like section adapted to adhere to the inner sheath, a urine collection section which covers the exposed meatus and functions as a surge chamber for voided urine and a tube section suitable for connection to a urine storage receptacle. The cap-like section, urine collection section and tube section of the outer sheath may be of unitary construction or, alternatively, may be separable components.

The inner sheath adheres to the penile skin by a pressure sensitive adhesive disposed on its interior surface. The outer sheath adheres to the inner sheath via a separate adhesive disposed on the interior surface of the outer sheath. The inner and outer sheaths are constructed of an elastomeric material such as urethane, silicone, thermoplastic, or synthetic polymeric material.

In the preferred embodiment, the inner sheath covers at least a portion of the glans penis. To this end, the inner sheath may be form fitted to the glans penis or, alternatively, may be substantially conical or hemispherical in shape. In another embodiment, the inner sheath covers at least a portion of the penile shaft and is substantially cylindrical in shape. In a still further embodiment, the inner sheath covers at least a portion of the glans penis and at least a portion of the penile shaft.

In accordance with one method of application of the inner and/or outer sheath, the user inverts the sheath, aligns the forward opening in the case of the inner sheath, or the cap-like portion in the case of the outer sheath, with the tip of the penis and then re-inverts the sheath to restore the sheath to its original orientation. In accordance with an alternative method of application of the inner and/or outer sheath, the sheath is provided with a rolled up rearward portion which is unrolled to cover a portion of the glans penis, penile shaft, or both, in the manner of a condom.

With the disclosed two-piece male incontinence device, the inner sheath functions as a semi-permanent protective layer which adheres to the penile skin, while the outer sheath adheres to the inner sheath to collect urine and transfer the urine to an attached collection receptacle via tubing. The user can change the outer sheath as needed while leaving the inner sheath intact for prolonged periods of time, thereby minimizing penile skin damage and erosion resulting from repeated removal of a device which is adhesively bonded to the skin. Furthermore, the described device maintains optimum positioning on the penis, in order to effectively and reliably collect urine. In particular, in the embodiment in which the inner sheath covers a portion of the glans penis, the inner sheath effectively "locks on" to the penis tip, thereby preventing movement of the penile skin relative to the device. In the embodiment in which the inner sheath covers a portion of the penile shaft, the resiliency of the material comprising the inner sheath results in less movement of the penile skin relative to the device than heretofore achieved with conventional condom catheters.

BRIEF DESCRIPTION OF THE DRAWINGS

The foregoing features of this invention, as well as the invention itself, may be more fully understood from the following detailed description of the drawings in which.

DESCRIPTION OF THE PREFERRED EMBODIMENT

Figure 1:
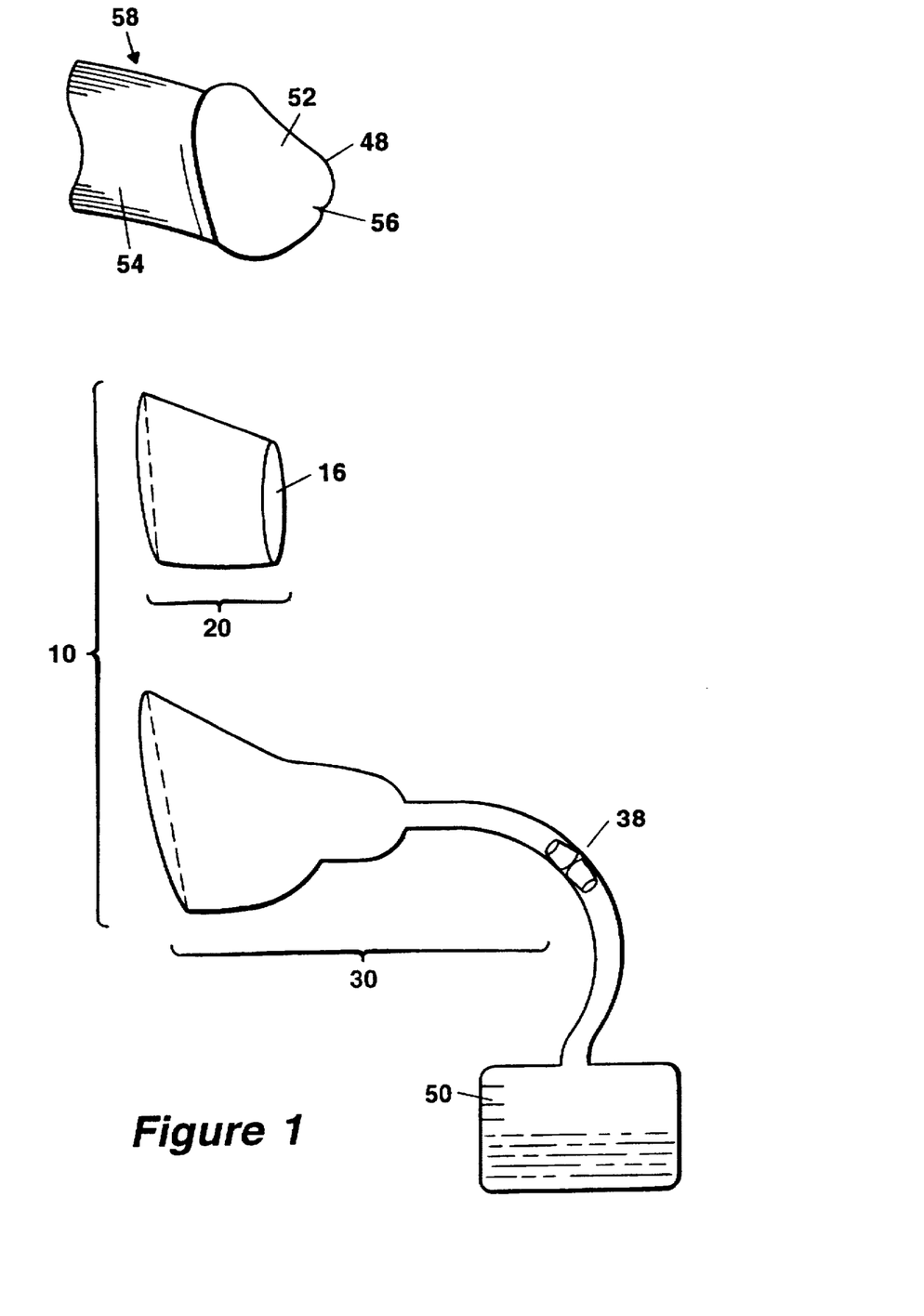
FIG. 1 shows an exploded view of a two-piece male incontinence device including inner and outer sheaths in accordance with the invention.

Referring to FIG. 1, a male incontinence device 10 includes: (1) an inner sheath 20 and (2) an outer sheath 30. The inner sheath 20 fits over and adheres to the glans penis 52 and/or the penile shaft 54 and includes an aperture, or opening 16 at a forward end for exposing the meatus 56 of the penis 58 of the user. The outer sheath 30 fits over and adheres to the inner sheath 20 and directs voided urine to a urine storage receptacle 50 coupled to the outer sheath by a connector 38.

Figure 5:
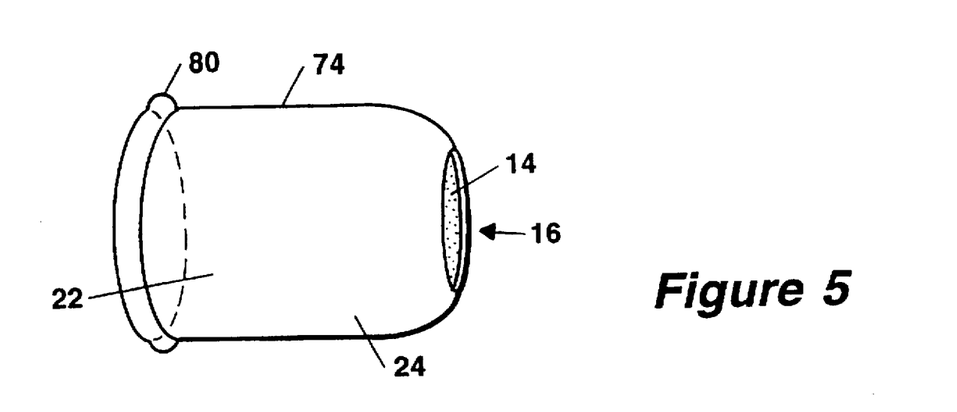
FIG. 5 is a perspective view of a substantially hemispherical shaped inner sheath embodiment of the male incontinence device.
Figure 6:
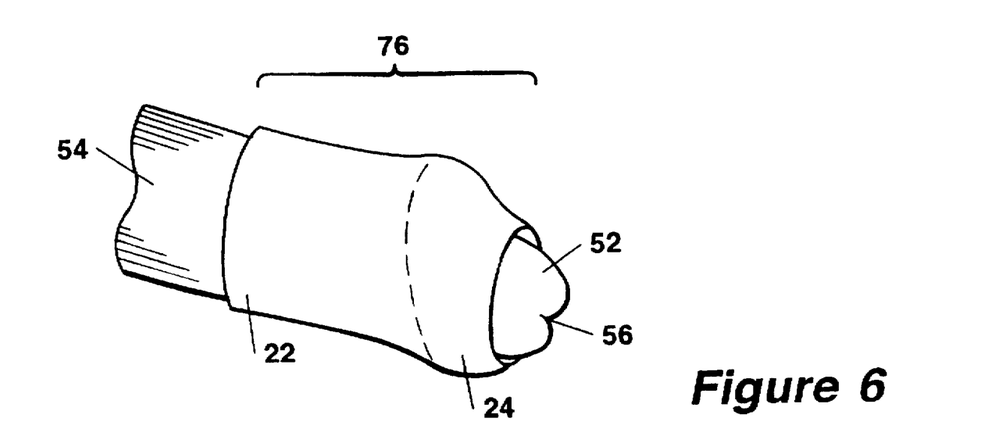
FIG. 6 is a perspective view of a further alternate embodiment of the inner sheath of the male incontinence device adapted to cover a portion of the penile shaft and a portion of the penile glans in use.

The inner sheath 20 may be any size or shape suitable for covering at least part of the glans penis 52 and/or penile shaft 54 of the user. FIGS. 2–6 show different embodiments of inner sheaths, in which like reference numbers refer to like features. In one embodiment shown in FIGS. 2, 2A and 2B, the inner sheath 20 is substantially form fitted to the shape of the glans penis 52. In another embodiment shown in FIG. 3, 3A, and 3B, the inner sheath 70 is substantially cylindrical to cover the penile shaft 54. In a still further embodiment shown in FIG. 4, the inner sheath 72 is substantially conical in shape to fit over at least a portion of the glans penis 52. The inner sheath 74, shown in FIG. 5, is substantially hemispherical in shape to fit over at least a portion of the glans penis 52. In the embodiment of FIG. 6, the inner sheath 76 is shaped to fit over a portion of the glans penis 52 and a portion of the penile shaft 54.

Features of the inner sheath embodiments of FIGS. 2–6 will be described generally with reference to illustrative sheath 20 of FIGS. 2, 2A and 2B. The inner sheath 20 has an interior surface 22 and an exterior surface 24. The interior surface 22 has an adhesive 14 disposed thereon for securely adhering the inner sheath 20 to the glans penis 52. Any medical grade pressure sensitive adhesive may be used, provided that is sufficient to secure the inner sheath 20 to the glans penis.

The adhesive 14 may be applied by the user when application of the inner sheath 20 is desired or, alternatively, may be provided on the interior surface 22 during manufacture. The exterior surface 24 of the inner sheath may or may not have an adhesive applied for the purpose of adhering to the outer sheath 30, as will be described. In the preferred embodiment, adhesive 14 is not applied to the exterior surface 24 of the inner sheath 20.

Figure 2:
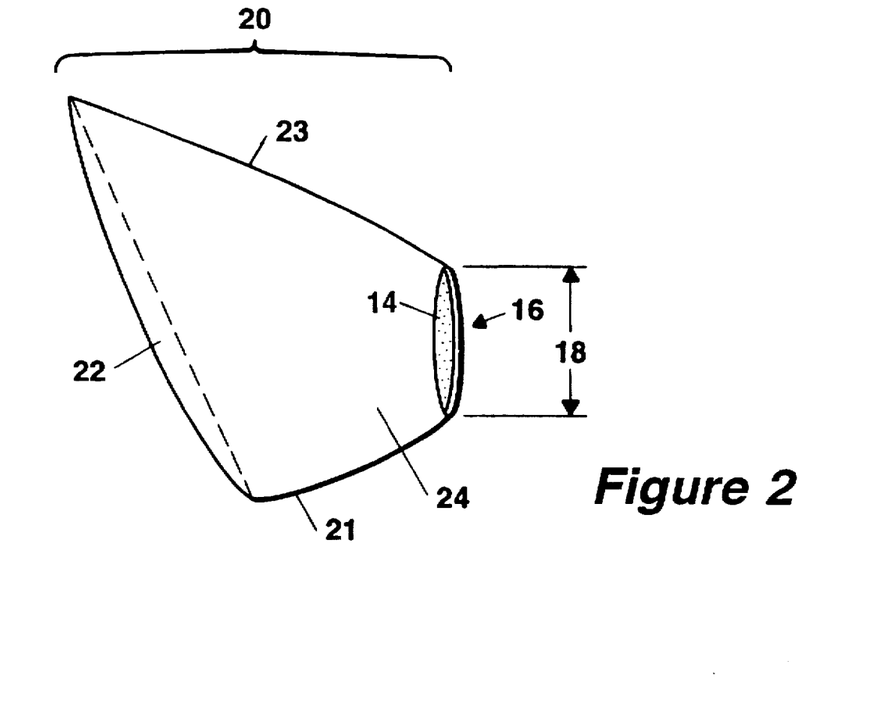
FIG. 2 is a perspective view of an embodiment of the inner sheath of the male incontinence device having a shape form fitted to the penile glans.
Figure 2A:
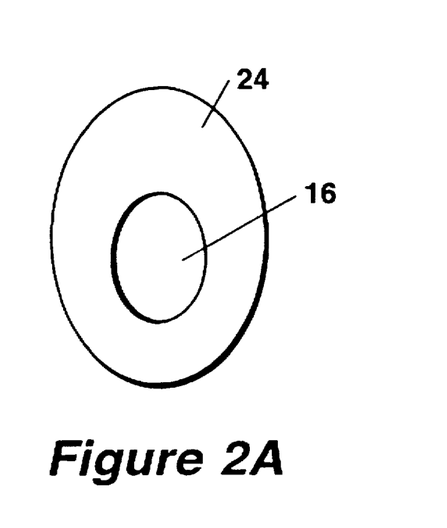
FIG. 2A is a front plan view of the inner sheath of FIG. 2.
Figure 2B:
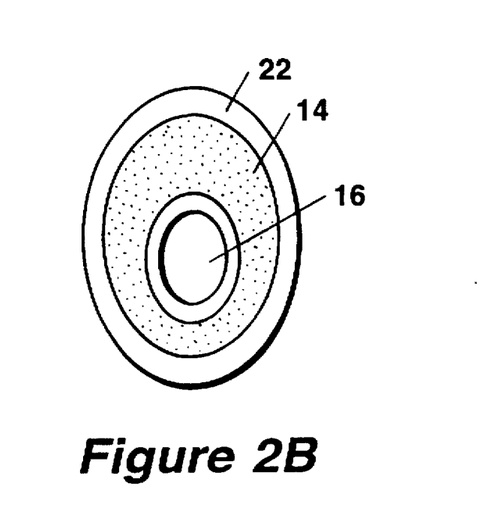
FIG. 2B is a rear plan view of the inner sheath of FIG. 2.

In the preferred embodiment shown in FIG. 2, the adhesive 14 covers substantially the entire interior surface 22. Alternatively however, the adhesive 14 may be provided in the form of a strip of adhesive disposed circumferentially around the interior surface 22 of the inner sheath.

Figure 3:
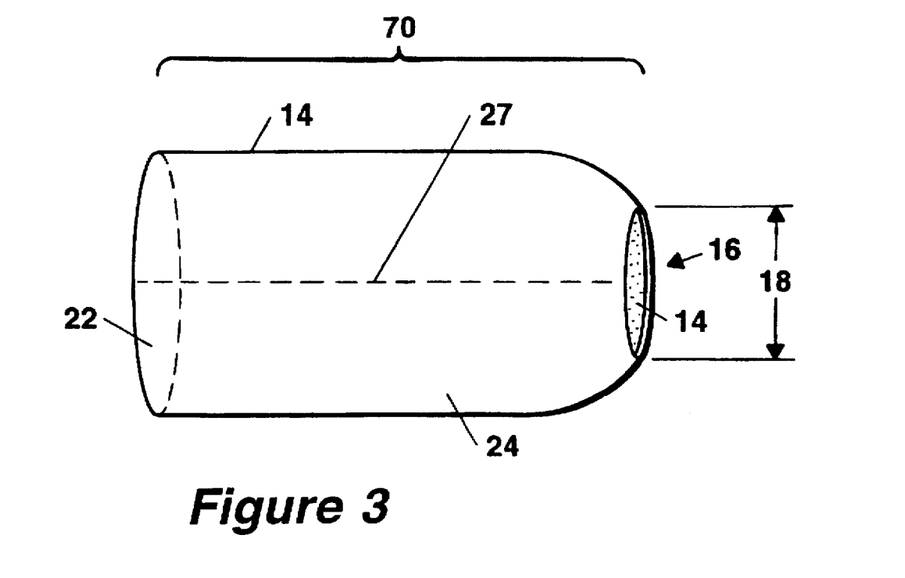
FIG. 3 is a perspective view of an alternate embodiment of the inner sheath of the male incontinence device having a substantially cylindrical shape to fit the penile shaft.
Figure 3A:
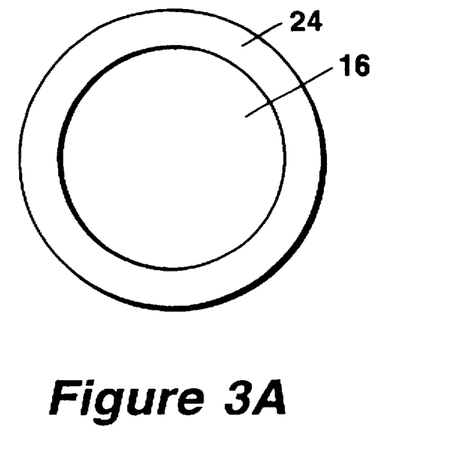
FIG. 3A is a front plan view of the inner sheath of FIG. 3.
Figure 3B:
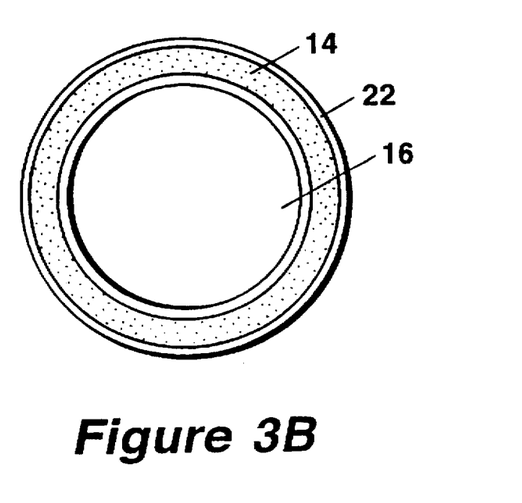
FIG. 3B is a rear plan view of the inner sheath of FIG. 3.
Figure 4:
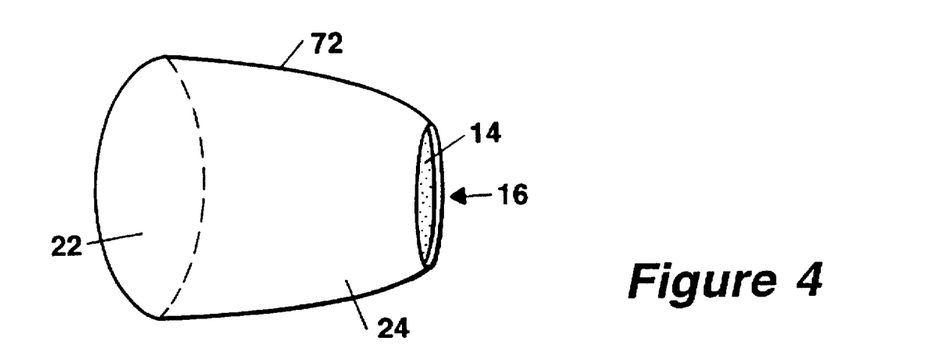
FIG. 4 is a perspective view of a substantially conical shaped inner sheath embodiment of the male incontinence device.

In use, the forward aperture, or opening 16 of the inner sheath 20 is aligned with the penile tip 48 and has a sufficient diameter, labelled 18, to expose the meatus 56. In the embodiment of FIG. 2, the diameter 18 of the aperture 16 permits the tip 48 of the penis to protrude through the opening 16, as is apparent by reference to FIG. 9. In the embodiments of FIG. 3, the aperture 16 has sufficient diameter 18 to permit the entire glans 52 of the penis to protrude therethrough.

The inner sheath 20 may be made of any rubber or flexible material and preferably medical grade thermoplastic elastomer, silicone, or urethane. Any material may suffice provided that it is resilient, durable, and waterproof. Preferably, the inner sheath 20 is constructed of Shore A 10–80 durometer medical grade thermoplastic elastomer or silicone.

With particular reference to FIG. 3, it is noted that the inner sheath 70 may be a continuous cylindrical member. Alternatively however, the inner sheath 70 may have perforations 27 permitting the sheath 70 to be "wrapped around" the penile shaft 54 alone or in combination with the glans 52 so as to join together along the axis of perforations 27, such as with adhesive.

In the preferred embodiment, the inner sheath 20 may be applied to the penis 58 of the user by an inversion technique described below in conjunction with FIG. 9. Alternatively however, the inner sheath may be unrolled in the manner of a condom onto the glans penis 52, penile shaft 54 or a portion of each depending on the particular embodiment. To this end, at least a portion 80 of the inner sheath is rolled up, as shown in the illustrative inner sheath embodiment of FIG. 5.

Figure 7:
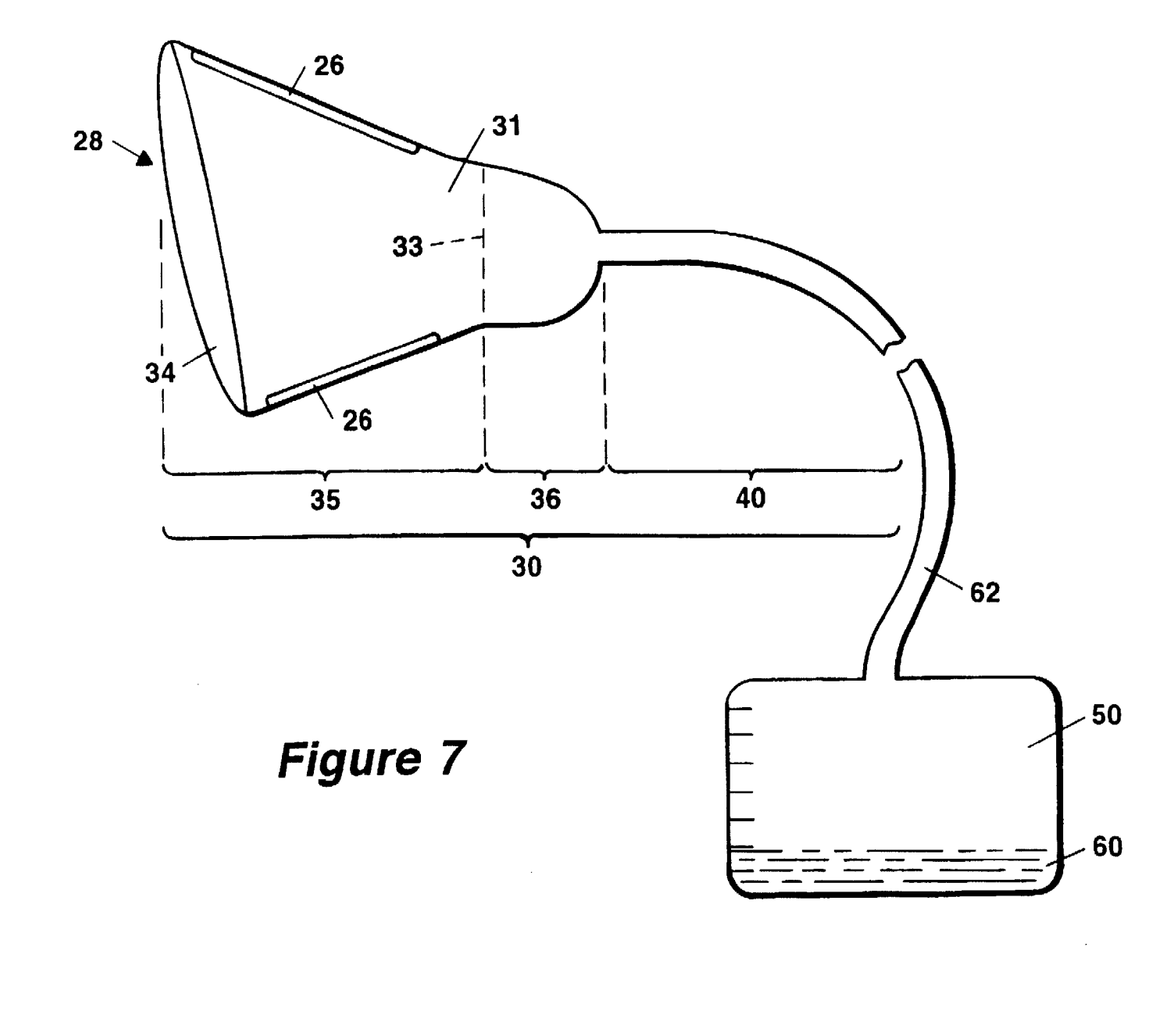
FIG. 7 is a partial cross-sectional view of an embodiment of the outer sheath of the male incontinence device having a shape form fitted to the penile glans.
Figure 8:
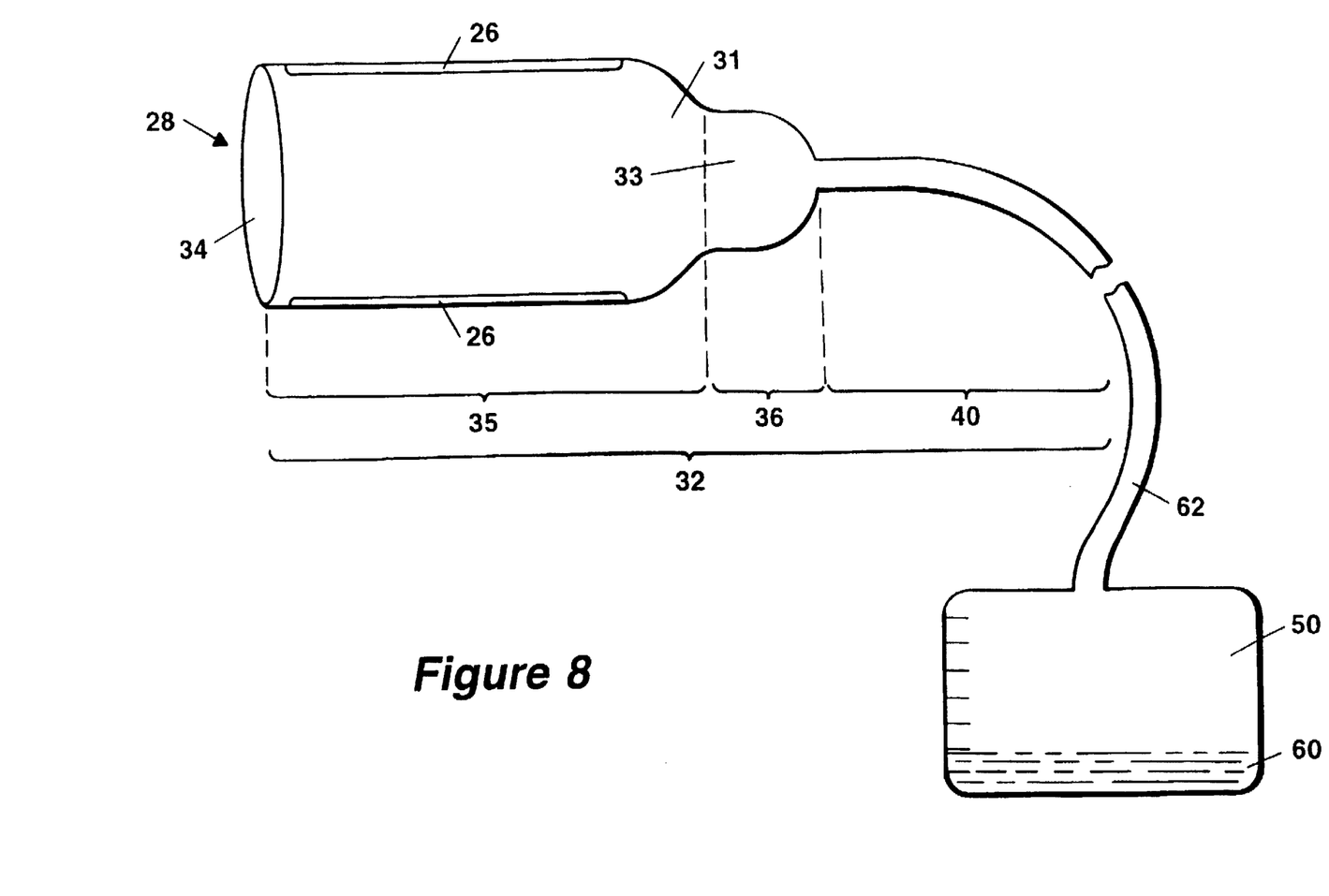
FIG. 8 is a partial cross-sectional view of an embodiment of the outer sheath of the male incontinence device having a cylindrical shape to cover the penile shaft and glans.

The outer sheath 30 may be of any size or shape suitable for covering the inner sheath. For example, one embodiment of an outer sheath 30, shown in FIG. 7, is particularly well suited for use with the inner sheath 20 of FIG. 2 and another embodiment of an outer sheath 32, shown in FIG. 8, is particularly well suited for use with the inner sheath 70 of FIG. 3. Each of the outer sheaths 30, 32 includes three continuous portions, or sections: (1) a cap-like section 35 that fits over and secures to the inner sheath 20, 70, respectively; (2) a urine collection section 36; and (3) a tube section 40. Outer sheaths 30 and 32 differ only in the shape of their respective cap-like sections 35. In particular, the cap-like section 35 of outer sheath 30 has a shape form fitted to the penile glans 52 like the shape of the associated inner sheath 20 (FIG. 2). The cap-like section 35 of outer sheath 32 has a substantially cylindrical shape like the shape of the associated inner sheath 70 (FIG. 3). Although the cap-like section 35 is preferably substantially the same shape as the associated inner sheath it will be appreciated that the shapes of the inner sheath and cap-like section of the associated outer sheath may differ. More generally, the cap-like section of the outer sheath is slightly larger than the associated inner sheath so as to cover the inner sheath in a liquid tight fashion.

Features of the outer sheath embodiments of FIGS. 7 and 8 will be described generally with reference to the illustrative outer sheath 30 of FIG. 7. The cap-like section 35 has an open proximal end 28, a narrower distal end 33, an interior surface 34 and an exterior surface 31. The wider open proximal end 28 fits over and secures to the exterior surface 24 of the inner sheath 20. To this end, an adhesive 26 is provided on the interior surface 34 of the cap-like section 35 which permits interior surface 34 of the outer sheath 30 to adhere to the exterior surface 24 of the inner sheath 20. The adhesive 26 may or may not be the same adhesive or adhesive strength as adhesive 14 on the interior surface of the inner sheath 20. Adhesive 26 need not be a medical grade pressure sensitive adhesive since it contacts the exterior surface 24 of the inner sheath 20 and not the user's skin. The adhesive 26 may cover substantially the entire interior surface 34 of the cap-like section 35 or may be disposed anywhere along the interior surface 34, such as in the form of a circumferential strip.

The cap-like section 35 of the outer sheath may be coupled to the inner sheath by the inversion technique described below in conjunction with FIG. 9 or the cap-like section of the outer sheath may be unraveled like a condom onto inner sheath 20. In the case where the cap-like section is unraveled onto the inner sheath, at least a portion of the cap-like section is rolled up, in the manner shown in conjunction with the illustrative inner sheath of FIG. 5.

The intermediate urine collection section 36 can be any shape, but, in the preferred embodiment, the urine collection section 36 is either oval or circular in cross-section. The urine collection section 36 serves as a surge chamber to capture voided urine and pass the urine to the tube section 40.

Tube section 40 consists of a circular tube that leads from the urine collection portion 36 to a urine receptacle 50, such as a bag, where urine 60 is stored. The tube section 40 can be any diameter or length sufficient to transmit the voided urine from the urine collection portion 36 to the receptacle 50.

The sections 35, 36 and 40 of the outer sheath 30 may be composed of the same or different materials. Furthermore, the outer sheath 30 and inner sheath 20 may be composed of the same or different materials. In the preferred embodiment, the outer sheath 30 and inner sheath 20 are composed of the same medical grade thermoplastic elastomer or silicone.

The cap-like section 35, urine collection section 36 and tube section 40 of the outer sheath 30 may be of unitary construction or, alternatively, may be separable components.

The tube portion 40 is coupled to the urine receptacle 50 and, more particularly to a tube portion 62 of the receptacle 50 via a connector 38, as shown in FIG. 1.

Application and use of the inner sheath 20 of FIG. 2 with the outer sheath 30 of FIG. 7 will now be described in conjunction with FIGS. 9 and 11. The user first applies the inner sheath 20 to the glans penis 52, making certain the broader surface 23 corresponds to the broader surface, or top portion of the glans while the smaller surface 21 corresponds to the undersurface of the glans. As is apparent, in the event that the inner sheath is substantially conical in shape as in the embodiment of FIG. 4 or substantially hemispherical in shape as in the embodiment of FIG. 5, no particular rotational orientation is necessary.

Figure 9:
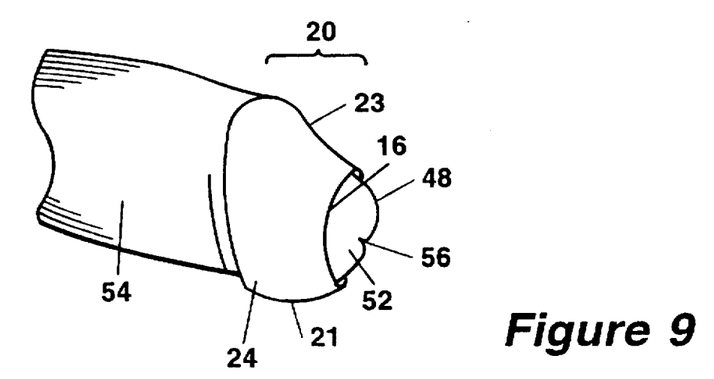
FIG. 9 illustrates the inner sheath of FIG. 2 in use.

The inner sheath 20 has two stable positions, a first position as shown in the FIG. 9 and a second position with the sheath inverted such that the exterior surface 24 is interior to the interior surface 22. In application, the user inverts the sheath 20 to the second position, brings the aperture 16 into alignment with the tip 48 of the penis so that the meatus 56 is at least exposed by the aperture. In the event that the adhesive 14 is to be applied by the user (as opposed to being applied during manufacture), the user then applies the adhesive 14 to the inner surface 22 of the sheath 20. Thereafter, the user re-inverts the inner sheath to its original position. The sheath is secured to the glans by applying pressure to the exterior surface 24 of the sheath 20 over the adhesive 14.

Figure 11:
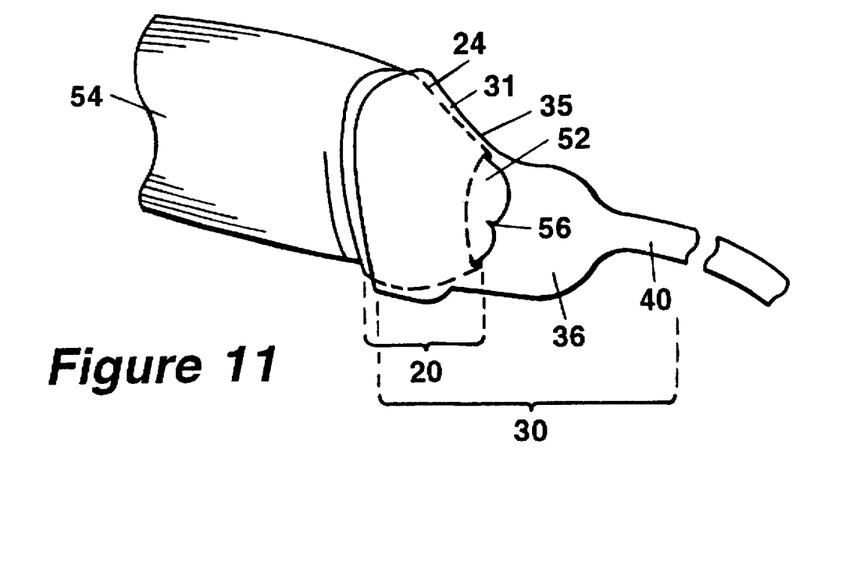
FIG. 11 illustrates use of the inner sheath of FIG. 2 along with the outer sheath of FIG. 7.

As shown in FIG. 11, the user then applies the cap-like portion 35 of the outer sheath 30 over the inner sheath 20, making certain that the outer sheath is orientated in a manner similar to the inner sheath 20. The cap-like portion 35 is then securely fastened to the inner sheath 20 with the adhesive 26 along the interior surface 34 of the cap-like portion 35 by applying pressure. The penile tip 48 is now housed in the urine collection portion 36. When the user voids, urine enters the urine collection portion 36. The urine then travels into tube section 40 and finally into the collection receptacle 50.

As is apparent, inner sheath 20 is secured to the skin with adhesive 14 while outer sheath 30 is secured to inner sheath 20 with adhesive 26. When the user desires to change the system, he can preferentially peel outer sheath 30 from inner sheath 20, leaving the inner sheath 20 in place attached to the penile glans. A new outer sheath 30 is then applied to the old inner sheath 20. In this fashion, inner sheath 20 can remain intact for a longer period of time, thereby preventing skin trauma and erosions resulting from repeated removal of a device adhesively bonded to skin. That is, since inner sheath 20 can stay in place for prolonged period of time, skin erosions and damage from repeat changes is minimized.

Figure 10:
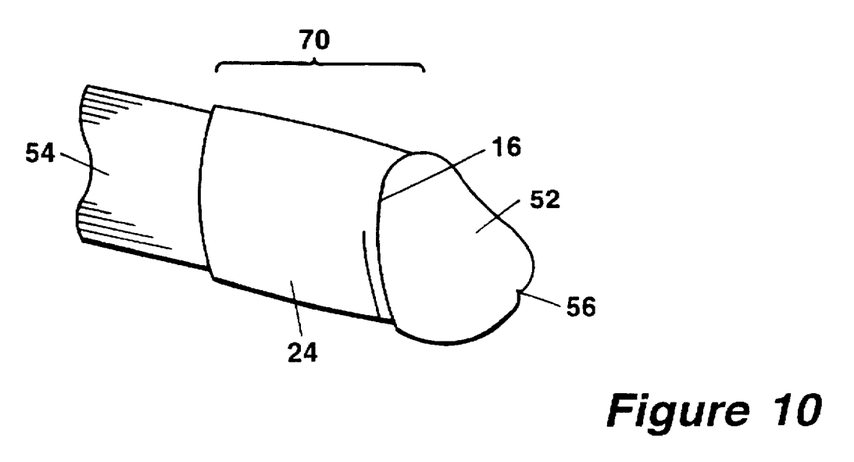
FIG. 10 illustrates the inner sheath of FIG. 3 in use.
Figure 12:
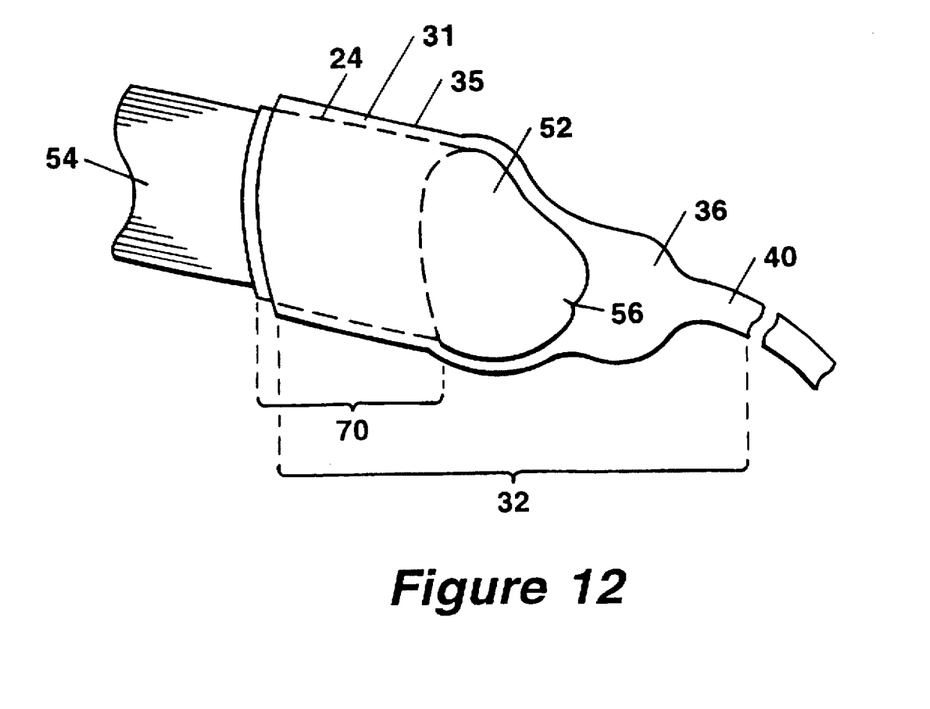
FIG. 12 illustrates use of the inner sheath of FIG. 3 along with the outer sheath of FIG. 8.

Referring to FIGS. 10 and 12, application and use of the inner sheath 70 of FIG. 3 with the outer sheath 32 of FIG. 8 will be described. The user applies the cylindrical shaped inner sheath 70 to the penile shaft 54 making certain a portion of, or the entire, glans penis 52 protrudes through opening 16. More specifically, the sheath 70 is inverted, brought into alignment with the penis 58 and then re-inverted to its original position such that the sheath covers at least a portion of the penile shaft 54.

As shown in FIG. 12, the outer sheath 32 is then applied to cover inner sheath 70 in a fashion similar to the above. In this embodiment, skin erosion on the shaft of the penis rather than the glans is minimized when the outer sheath 32 is changed, leaving inner sheath 70 intact.

Having described the preferred embodiments of the invention, it will now become apparent to one of skill in the art that other embodiments incorporating their concepts may be used. It is felt therefore that these embodiments should not be limited to disclosed embodiments but rather should be limited only by the spirit and scope of the appended claims.

We claim:

1. A male incontinence device comprising:
   an inner sheath adapted for adhering with an adhesive to a portion of the penis of a user and having an aperture for exposing the meatus of the penis; and
   an outer sheath adapted for adhering to said inner sheath in order to direct urine to a receptacle wherein the outer sheath is removable independently of the inner sheath.

2. The male incontinence device recited in claim 1 wherein said outer sheath comprises:
   a cap portion adapted for adhering to said inner sheath;
   a urine collection portion adjacent to said cap portion; and
   a tube portion adjacent to said urine collection portion for directing urine to said receptacle.

3. The male incontinence device recited in claim 2 wherein said cap portion of said outer sheath further comprises an adhesive disposed on an interior surface thereof.

4. The male incontinence device recited in claim 3 wherein said cap portion of said outer sheath has at least a portion which is rolled up and which is applied to said inner sheath by unrolling said rolled up portion over said inner sheath.

5. The male incontinence device recited in claim 1 wherein said inner sheath is adapted for adhering to at least a portion of the glans penis of said user.

6. The male incontinence device recited in claim 1 wherein said inner sheath is adapted for adhering to at least a portion of the penile shaft of said user.

7. The male incontinence device recited in claim 1 wherein said inner sheath is adapted for adhering to at least a portion of the glans penis and to at least a portion of the penile shaft of said user.

8. The male incontinence device recited in claim 1 wherein said inner sheath has a shape which is form fitted to at least a portion of said glans penis of said user.

9. The male incontinence device recited in claim 1 wherein said inner sheath is substantially conical in shape.

10. The male incontinence device recited in claim 1 wherein said inner sheath is substantially hemispherical in shape.

11. The male incontinence device recited in claim 1 wherein said inner sheath and said outer sheath are comprised of an elastomeric material.

12. The male incontinence device recited in claim 11 wherein said elastomeric material is selected from the group consisting of: urethane, silicone, thermoplastic and synthetic polymer.

13. The male incontinence device recited in claim 1 wherein said inner sheath further comprises an adhesive disposed on an interior surface thereof.

14. A male incontinence device comprising:
   an inner sheath adapted for adhering to a portion of the penis of a user and having an aperture for exposing the meatus of the penis; and
   an outer sheath adapted for adhering to said inner sheath in order to direct urine to a receptacle, said outer sheath comprising:
   a cap portion adapted for adhering to said inner sheath;
   a urine collection portion adjacent to said cap portion; and
   a tube portion adjacent to said urine collection portion for directing urine to said receptacle.

15. A male incontinence device comprising:
   an inner sheath adapted for adhering with an adhesive to a portion of the penis of a user and having an aperture at a forward end thereof for exposing the meatus of said penis; and
   an outer sheath comprising a cap portion adapted for adhering to said inner sheath and a urine collection portion in fluid communication with said cap portion for receipt of urine.

16. The male incontinence device recited in claim 15 wherein said inner sheath is adapted for adhering to at least a portion of the glans penis of said user.

17. The male incontinence device recited in claim 15 wherein said inner sheath is adapted for adhering to at least a portion of the penile shaft of said user.

18. A method for collection of urine resulting from male incontinence comprising the steps of:
   applying an inner sheath having an aperture in a forward end to the penis of a user so that said aperture is aligned with the meatus of the penis; and
   adhering an outer sheath to said inner sheath, wherein said outer sheath directs urine toward a urine receptacle,
   wherein said inner sheath has an interior surface and an exterior surface and said inner sheath applying step comprises the steps of:
   inverting said inner sheath;
   placing said inner surface of said inner sheath adjacent to the penis of said user so that said aperture is aligned with the meatus of the penis; and
   inverting said inner sheath in order to restore said inner sheath to its original orientation in which said inner sheath covers at least a portion of said penis of said user.

19. A method for collection of urine resulting from male incontinence comprising the steps of:
   applying an inner sheath having an aperture in a forward end to the penis of a user so that said aperture is aligned with the meatus of the penis; and
   adhering an outer sheath to said inner sheath, wherein said outer sheath directs urine toward a urine receptacle and is removable independently of the inner sheath.

20. The method recited in claim 19 wherein a cap portion of said outer sheath is adhered to said inner sheath.

21. The method recited in claim 20 wherein said outer sheath is adhered to said inner sheath such that the tip of said penis is disposed in a urine collection portion of said outer sheath, said urine collection portion being disposed between said cap portion of said outer sheath and a tube portion of said outer sheath.

22. A combination of a male incontinence device, tubing and collection receptacle comprising:
   an inner sheath adapted for adhering with an adhesive to a portion of the penis of a user and having an aperture at a forward end thereof for exposing the meatus of said penis;
   an outer sheath comprising a cap portion adapted for adhering to said inner sheath and a urine collection portion in fluid communication with said cap portion for receipt of urine;
   a urine receptacle; and
   a tube in fluid communication between said cap portion and said urine receptacle.

* * * * *